US00RE50572E

(19) United States
(12) Reissued Patent
Cronin et al.

(10) Patent Number: US RE50,572 E
(45) Date of Reissued Patent: Sep. 2, 2025

(54) WEARABLE HEALTH INTERFACE FOR CONTROLLING INTERNET OF THINGS DEVICES

(71) Applicant: KONINKLIJKE PHILIPS N.V., Eindhoven (NL)

(72) Inventors: John Cronin, Bonita Springs, FL (US); Christopher Huffines, Bonita Springs, FL (US)

(73) Assignee: Koninklijke Philips N.V., Eindhoven (NL)

(21) Appl. No.: 17/380,161

(22) Filed: Jul. 20, 2021

Related U.S. Patent Documents

Reissue of:
(64) Patent No.: 10,359,807
Issued: Jul. 23, 2019
Appl. No.: 15/556,650
PCT Filed: Mar. 7, 2016
PCT No.: PCT/EP2016/054787
§ 371 (c)(1),
(2) Date: Sep. 8, 2017
PCT Pub. No.: WO2016/142338
PCT Pub. Date: Sep. 15, 2016

U.S. Applications:
(60) Provisional application No. 62/130,171, filed on Mar. 9, 2015.

(30) Foreign Application Priority Data

Jul. 20, 2015 (EP) ..... 15177443

(51) Int. Cl.
*G06F 1/16* (2006.01)
*A61B 5/00* (2006.01)
*A61B 5/0205* (2006.01)
*H04L 67/12* (2022.01)
*H04W 4/80* (2018.01)

(52) U.S. Cl.
CPC ..... *G06F 1/163* (2013.01); *A61B 5/0002* (2013.01); *A61B 5/02055* (2013.01); *A61B 2562/16* (2013.01); *H04L 67/12* (2013.01); *H04W 4/80* (2018.02)

(58) Field of Classification Search
CPC . B23K 20/023; A61B 2562/16; A61B 5/0002; A61B 5/02055; G06F 1/163; H04L 67/12; H04L 67/125; H04W 4/80
See application file for complete search history.

(56) References Cited

U.S. PATENT DOCUMENTS 9,682,622 B2 * 6/2017 Kim ..... G08B 21/06
10,798,547 B2 * 10/2020 Gold ..... G06Q 30/0207
(Continued)

FOREIGN PATENT DOCUMENTS

EP 2876907 A1 5/2015

*Primary Examiner* — Peng Ke

(57) ABSTRACT

A system and method enabling a wearable device to control an Internet of Things device. The wearable device includes at least one sensor, a communications interface configured to transmit an action command to the Internet of Things device in response to a triggering event, and a processor configured to analyze sensor data and determine whether a triggering event has occurred. When a triggering event occurs, the wearable device transmits an action command to control the Internet of Things device.

20 Claims, 15 Drawing Sheets

(56) References Cited

U.S. PATENT DOCUMENTS

| | | | | |
|---|---|---|---|---|
| 2014/0368336 | A1* | 12/2014 | Felix | H04W 4/90<br>340/539.13 |
| 2015/0035680 | A1 | 2/2015 | Li et al. | |
| 2015/0057808 | A1* | 2/2015 | Cook | G05B 13/04<br>700/275 |

* cited by examiner

252

| Sensor | Data Type | Date | Time | Datum |
|---|---|---|---|---|
| Pulse Oximeter | Pulse | 2-3-2015 | 1113 | 99 |
| Pulse Oximeter | Blood Pressure | 2-3-2015 | 1113 | 110/80 |
| Accelerometer | Motion | 2-3-2015 | 1115 | Accel020315 1115.dat |
| Accelerometer | Steps | 2-3-2015 | 1115 | 268 |
| ... | | | | |

FIG. 4

256

| Data Type | Wearable App | Wearable App Filename | IoT Device | Action Command |
|---|---|---|---|---|
| Sleep | NoDoze Driving | C:\\System\Apps\Nodozedriver.app | Ford F150 #651265189156 5 | Lock out car. |
| Accelerometer Pulse | Shower Starter | C:\\System\Apps\Showerstarter.app | Delta Spa System #987654123156 4 | Start post-workout shower. |
| ... | | | | |

FIG. 6

| Action Command | Wearable ID | Device Commands | Actuator ID |
|---|---|---|---|
| Start post-workout shower | FitBit JC4567 | Start now | In line Hot Water Heater |
| Start post-workout shower | FitBit JC4567 | Start +5 minutes | Shower faucet |
| ... | | | |

WEARABLE HEALTH INTERFACE FOR CONTROLLING INTERNET OF THINGS DEVICES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATION DATA

This application is the U.S. National Phase application under 35 U.S.C. § 371 of International Application No. PCT/EP2016/054787, filed on Mar. 7, 2016, which claims the benefit of European Application No. 15177443.7, filed Jul. 20, 2015, and Provisional Application Ser. No. 62/130,171, filed Mar. 9, 2015. These applications are hereby incorporated by reference herein.

FIELD OF THE INVENTION

The present disclosure generally relates to the field of wearable devices. In particular, the present disclosure is directed to a wearable health interface for controlling Internet of Things devices.

BACKGROUND

The Internet of Things is the network of physical objects that enables the collection and exchange of data. Any object capable of communicating data to a network can be a component of the Internet of Things, including but not limited to vehicles, smartphones, appliances, thermostats, lighting fixtures, and many more objects. Objects within the Internet of Things network typically include one or more sensors to obtain information, and a wired or wireless communication system that enables communication of the sensor data to the network.

Some current-generation wearable technology devices, such as smartwatches, fitness bands, and health wearables, for example, include one or more sensors for measuring various conditions or states of the wearer. Such sensors include pulse sensors for measuring the wearer's pulse, temperature sensors for measuring the wearer's temperature, and accelerometers for measuring the wearer's movement. However, current-generation wearable technology devices are limited in their usefulness, because they are typically only capable of being used within certain software and hardware environments, which are usually defined by a particular manufacturer. Consequently, users are not able to use wearable devices to their full potential. Additionally, current-generation wearable technology devices are only able to communicate with other devices, such as objects within the Internet of Things, if the devices are specifically pre-programmed or designed to communicate. This significantly limits the number of devices that wearable technology devices can communicate with, and thus inhibits the potential functionality of wearable technology devices.

Accordingly, there is a continued need in the art for wearable technology devices that can communicate and interact with other objects within the Internet of Things.

SUMMARY

The present disclosure is directed to inventive methods and systems for enabling a wearable device to control an Internet of Things device. By utilizing various aspects of this disclosure, users can define relationships between wearable device sensor readings and various Internet of Things devices. For example, a user may configure one or more wearable devices using the teachings herein to activate a shower when a certain level of sweat is detected on the user's body. Similarly, a user may configure a wearable device to activate a cleaning device when the user is experiencing a certain amount of fatigue. By enabling direct control of Internet of Things devices via a wearable device, complicated and proprietary hardware can be avoided, allowing users to use wearable devices to a fuller potential.

In one implementation, the present disclosure is directed to a method of enabling a wearable device to control an Internet of Things device, the method being implemented on a wearable device. The method comprises: receiving sensor data from one or more wearable sensors; executing one or more wearable apps as a function of the sensor data to produce one or more action commands; and transmitting one or more device commands to an Internet of Things device as a function of the one or more action commands.

In another implementation, the present disclosure is directed to a machine-readable storage medium containing machine-executable instructions for performing a method of enabling a wearable device to control an Internet of Things device, the method being implemented on a wearable device. The method comprises: receiving sensor data from one or more wearable sensors; executing one or more wearable apps as a function of the sensor data to produce one or more action commands; and transmitting one or more device commands to an Internet of Things device as a function of the one or more action commands.

According an aspect is a method for controlling an Internet of Things device using a wearable device. The method includes the steps of: (i) providing a wearable device comprising at least one sensor, a processor, a wearable application database including one or more wearable applications, and a communications interface; (ii) receiving sensor data from the at least one sensor; (iii) selecting, based on the received sensor data, at least one of the one or more wearable applications in the wearable application database to analyze the received sensor data; (iv) analyzing the received sensor data with the selected wearable application to determine whether the received sensor data comprises a triggering event; (v) generating, if the received sensor data comprises a triggering event, an action command for a remote Internet of Things device; and (vi) transmitting the action command to the remote Internet of Things device.

According to an embodiment, the method further includes the step of receiving, from a user, input regarding which of the one or more wearable applications in the wearable application database to use to analyze the received sensor data.

According to an embodiment, the wearable device further includes a wearable device ID, and wherein the method further comprises the step of communicating the wearable device ID.

According to an embodiment, the action command includes a command to control one or more of: a light, a lock, a thermostat, a food preparation device, a cleaning device, a first responder emergency call, an appliance, a reward item, exercise equipment, and a shower.

According to an embodiment, the at least one sensor comprises a GPS, a camera, a pulse oximeter, a temperature sensor, an accelerometer, or a galvanic skin sweat sensor.

According to an embodiment, the method further includes the step of downloading, from an application network, a wearable application to the wearable device.

According to an embodiment, the method further includes the step of downloading, from an application database of the Internet of Things device, a wearable application to the wearable device.

According to an aspect is a system for controlling an Internet of Things device using a wearable device. The system includes: an application network comprising an application network database comprising one or more wearable applications, and a communications interface; an Internet of Things device comprising a wearable application database comprising one or more wearable applications, a communications interface, and an actuator; and a wearable device comprising at least one sensor, a processor, a wearable application database comprising one or more wearable applications, and a communications interface, wherein the wearable device is configured to: (i) select, based on the received sensor data, at least one of the one or more wearable applications in the wearable application database to analyze the received sensor data; (ii) analyze the received sensor data with the selected wearable application; (iii) generate, if the received sensor data comprises a triggering event, an action command for the Internet of Things device; and (iv) transmit the action command to the Internet of Things device.

According to an embodiment, the wearable device is further configured to establish communication with the application network, and download a wearable application from the application network database.

According to an embodiment, the wearable device is further configured to establish communication with the wearable application database of the Internet of Things device, and download a wearable application.

According to an embodiment, the wearable device comprises a user interface configured to receive input from a user.

According to an embodiment, the Internet of Things device is configured to activate the actuator in response to receiving the action command from the wearable device.

According to an embodiment, the Internet of Things device is configured to determine, based on the action command transmitted by the wearable device, whether to activate the actuator.

According to an aspect is a wearable device configured to control a remote Internet of Things device. The wearable device includes: at least one sensor; a communications interface configured to transmit an action command to the remote Internet of Things device in response to a triggering event; a wearable application database comprising one or more wearable applications; and a processor, wherein the processor is configured to: (i) receive sensor data from the at least one sensor; (ii) select, based on the received sensor data, at least one of the one or more wearable applications from the wearable application database to analyze the received sensor data; (iii) analyze the received sensor data with the selected wearable application; (iv) generate, if the received sensor data comprises a triggering event, an action command for the Internet of Things device; and (iv) induce the communications interface to transmit the action command to the Internet of Things device.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). As used herein, the term "non-transitory machine-readable medium" will be understood to encompass both volatile and non-volatile memories, but to exclude transitory signals. In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

In one network implementation, one or more devices coupled to a network may serve as a controller for one or more other devices coupled to the network (e.g., in a master/slave relationship). In another implementation, a networked environment may include one or more dedicated controllers that are configured to control one or more of the devices coupled to the network. Generally, multiple devices coupled to the network each may have access to data that is present on the communications medium or media; however, a given device may be "addressable" in that it is configured to selectively exchange data with (i.e., receive data from and/or transmit data to) the network, based, for example, on one or more particular identifiers (e.g., "addresses") assigned to it.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. It should be understood that the present disclosure is not limited to the precise arrangements and instrumentalities shown in the drawings, wherein:

FIG. 4 is an example of a wearable sensor database, in accordance with an embodiment.

FIG. 6 is an example of a wearable app match database, in accordance with an embodiment.

DETAILED DESCRIPTION

Applicant has recognized and appreciated that there is a need for wearable devices to be able to trigger Internet of Things ("IoT") devices based on wearable sensor data. Accordingly, the present disclosure is directed to inventive methods and systems enabling a wearable to download, e.g., through an application programming interface ("API") or app store, software associated with any Internet of Things device, where the Internet of Things device uses the wearable-standard format and communications. The system enables automatic connection between the wearable and the Internet of Things device, and the wearable can trigger actions of the Internet of Things device based on its sensory readings. In some embodiments, such software may be downloaded in the form of one or more applications (or "apps") and/or may be downloaded from a health data network.

Figure 1:
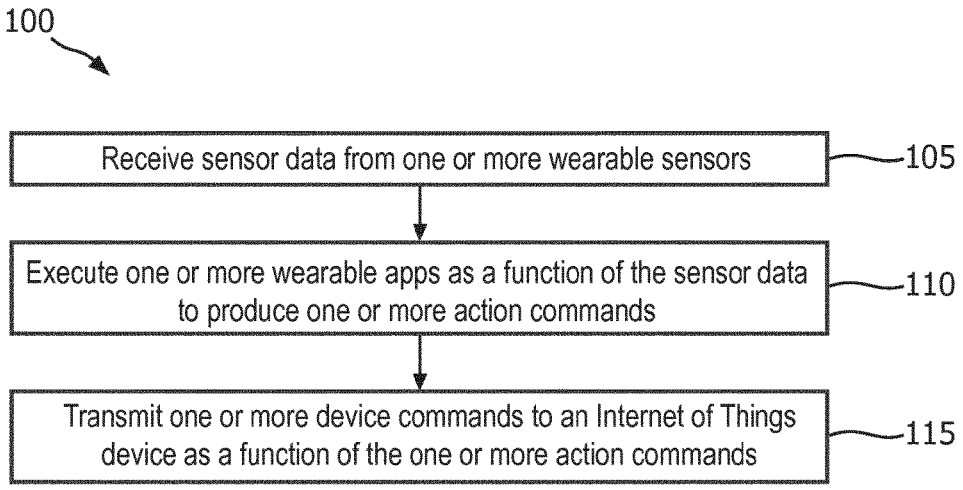
FIG. 1 is a flowchart of a method for utilizing a wearable health interface to control Internet of Things devices, in accordance with an embodiment.

At a high level, aspects of the present disclosure are directed to systems, methods, and software for controlling Internet of Things devices via a wearable device interface. According to an embodiment, users may specify triggers that specify when and how data derived from wearable devices should lead to activation or control of Internet of Things devices. Referring to FIG. 1, in one embodiment, is a method 100 that may be used with a wearable health interface for controlling Internet of Things devices, which may comprise a step 105 of receiving sensor data from one or more wearable sensors, a step 110 of executing one or more wearable apps as a function of the sensor data to produce one or more action commands, and a step 115 of transmitting one or more device commands to an Internet of Things device as a function of the one or more action commands.

Receiving sensor data from one or more wearable sensors at step 105 may comprise receiving any type of sensor data from any type of wearable sensor. For example, a heart rate sensor may provide readings of a user's heart rate in beats per minute, a temperature sensor may provide readings of a user's temperature in degrees Fahrenheit, and/or a pedometer may provide readings corresponding to a number of steps a user has taken, among other types of sensor data.

Executing one or more wearable apps as a function of the sensor data to produce one or more action commands at step 110 may comprise comparing readings received from one or more wearable sensors to predetermined triggers. Such triggers may specify that, for example, a particularly high reading of a user's temperature, which may indicate fever, should cause a thermostat to increase its temperature to help the user overcome the fever, or lower the thermostat to make the user more comfortable. Transmitting one or more device commands to an Internet of Things device as a function of the one or more action commands at step 115 may comprise recognizing that a trigger specifies that, e.g., a particularly high reading of a user's temperature should cause a thermostat to increase its temperature to help the user overcome the fever and, based on that recognition, transmitting a device command to a smart thermostat to cause it to increase ambient air temperature. By using a system like the embodiment depicted in FIG. 2 to implement a method like that of FIG. 1, users can quickly and easily control Internet of Things devices via a wearable device interface.

Figure 2:
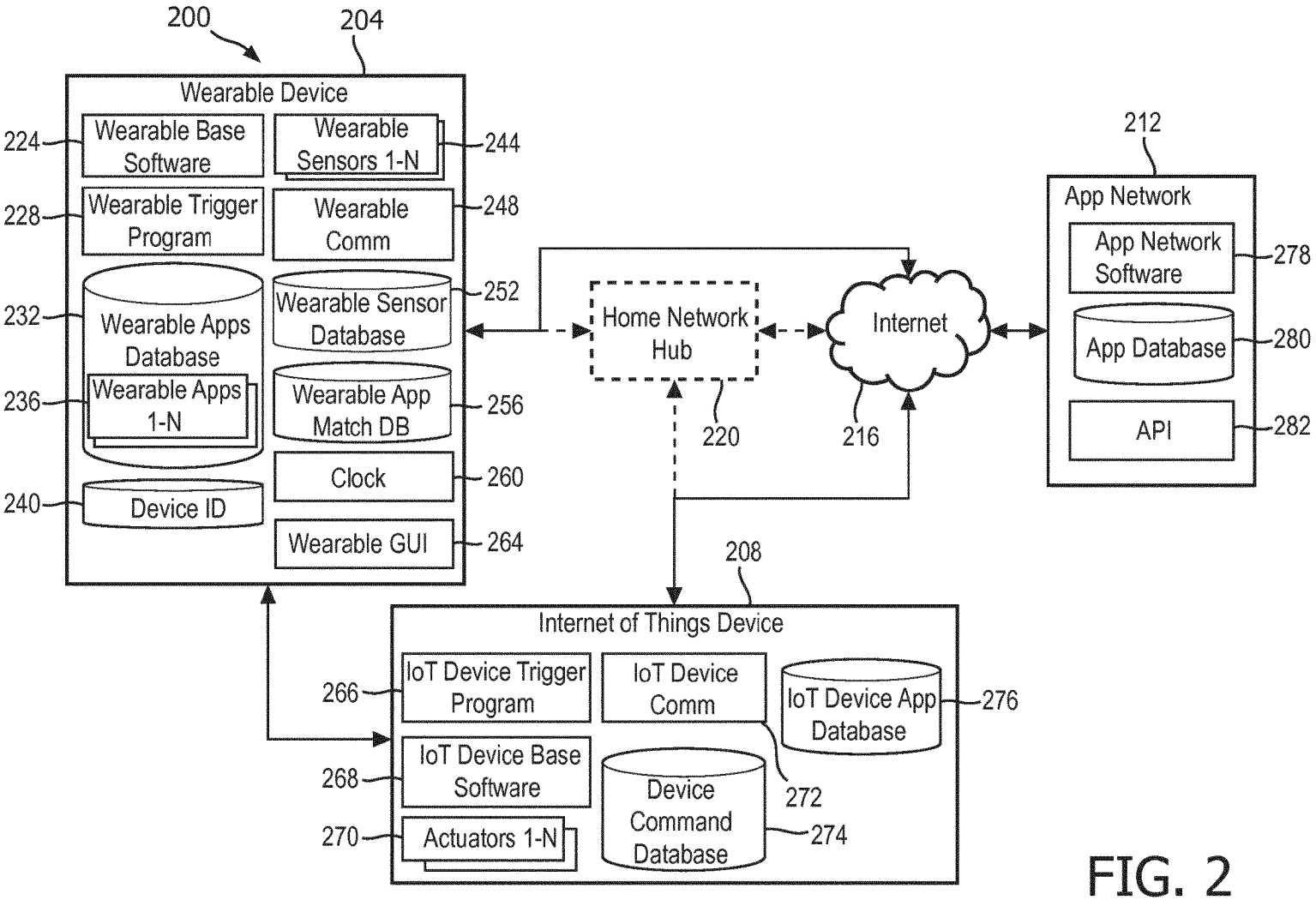
FIG. 2 is a schematic representation of a system including a wearable health interface for controlling Internet of Things devices, in accordance with an embodiment.

Referring to FIG. 2, in one embodiment, is a system 200 that may be used to implement one or more steps of the method of FIG. 1 and includes a wearable device and interface for controlling one or more Internet of Things devices. System 200 may comprise, for example, a wearable device 204, an Internet of Things device 208, and an application network 212. Each component may be connected to each other through the Internet 216, and these connections may comprise any suitable form of digital communication such as 3G, 4G, and/or 5G cellular, Wi-Fi™, and/or TCP/IP or other wired Internet connections, among others. The wearable device 204 and Internet of Things device 208 may communicate directly via any suitable means, and in some embodiments they may communicate to each other and/or to the Internet 216 through a home network hub 220 or gateway device, which intermediates between the entire Internet of Things home network and the Internet 216 and which may be a device such as a router, firewall, and/or a central hub, among other devices.

According to an embodiment, wearable device 204 is a device worn or carried by an individual or by another living thing, such as a pet, which records data about the wearer and/or his environment. Based on that data, wearable device 204 may take certain actions and/or send certain commands. Wearable device 204 may comprise wearable base software 224, which is the basic software the wearable device runs that controls its various operable pieces. Wearable device 204 may further comprise a wearable trigger program 228, which is a software program that governs whether or not, and when, data will be sent to the home network hub 220, the Internet 216, the Internet of Things device 208, and/or a wearable apps database 232. Wearable apps database 232 is a database containing wearable applications, or "apps," 1 through N 236 that may be stored on and/or executed by a wearable device. In some embodiments, one or more wearable apps 236 may determine whether or not particular sensor data warrants sending a command to an Internet of Things device 208. Wearable device 204 may further comprise a device identifier ("ID") 240, which may be a unique ID associated with each wearable device that allows the wearable device to be identified. Wearable device 204 may further comprise wearable sensors 1 through N 244, which may be sensors that record data associated with the wearer or the wearer's environment. Sensors 244 may include, but are not limited to, sensors such as pulse oximeter sensors, which can detect pulse, blood pressure, and blood oxygen level. Sensors 244 may detect the wearer's temperature, the wearer's movement, the wearer's location, ambient noise levels, humidity levels, ambient carbon monoxide, oxygen, and other gas levels, the ambient temperature, a level of particulate matter, and/or light levels, among many others.

Wearable device 204 may further include a wearable communications interface 248, or "comm," which is a communications module that may utilize Bluetooth, low-power Bluetooth, 3G, 4G, 5G, Wi-Fi™, laser, visible, infrared, microwave, and/or any other suitable method for communicating wirelessly and/or via a wired connection such as an Ethernet port, a USB port, etc. Wearable device 204 may also include a wearable sensor database 252, which may contain data generated by wearable sensors 1 through N 244, and a wearable app match database 256 that software may utilize to determine which of the wearable apps 1 through N 236 should be applied to the data generated by wearable sensors 1 through N 244. As shown in FIG. 2, the wearable device 204 may also include a clock 260 for recording date and time and a wearable graphical user interface or "GUI" 264 that can be used to input or view data on the wearable device.

Wearable device 204 may also comprise a processor 246 configured or programmed to perform various functions discussed herein, and can be utilized in combination with a memory comprising one or more sets of instructions executable by processor 246, and which cause the wearable device 204 and/or system 200 to execute one or more of the steps of the methods described herein. According to an embodiment, processor 246 is in communication with sensors 244 to obtain and/or store sensor data. Processor 246 can also be in communication with and execute one or more modules or components of wearable base software 224, wearable trigger program 228, and wearable apps 232. The processor can also facilitate communication with home network hub 220, Internet 216, Internet of Things device 208, and/or wearable apps database 232, via wearable communications interface 248.

According to an embodiment, Internet of Things device 208 is a device connected to the Internet of Things, a set of hitherto dumb devices, which by virtue of being Internet of Things devices are equipped with the mechanisms to interact intelligently with the Internet and/or with other devices. Accordingly, for example, a "dumb" refrigerator may be manufactured with and/or retrofitted to be an Internet of Things refrigerator and to have smart functionality to allow it to scan its surroundings, its contents, communicate with one or more users, etc. In some embodiments, Internet of Things device 208 may be something that is a possession of but not necessarily wearable by a user. According to an embodiment, Internet of Things device 208 executes an Internet of Things device trigger program 266, which is a program that receives and passes on one or more triggers and/or action commands that are sent from wearable trigger program 228. Internet of Things device base software 268 is the software that governs the device's general operations. Actuators 1 through N 270 of the Internet of Things device are any device, component, or mechanism by which Internet of Things device 208 may take an action. For example, in the context of a refrigerator, such actuators 270 may comprise a mechanism that may open and/or close the door, activate the icemaker, and/or adjust the temperature inside the refrigerator or freezer component. Actuator 270 may comprise, for example, a display on the inside or outside of the refrigerator and a sensor inside the refrigerator. Internet of Things device communications interface 272 is a communications module that may be identical to, or different from, wearable communications interface 248. The device command database 274 is a database that correlates action commands sent from wearable device 204 to specific commands and/or specific actuators 270 in Internet of Things device 208 and is further described in the context of FIG. 13 below. Internet of Things device app database 276 contains apps that the wearable device 204 may download and store as one or more wearable apps 1 through N 236. According to an embodiment, wearable apps 236 stored in or available from the Internet of Things device app database 276 can be specific to interacting with and/or controlling Internet of Things device 208, although other app functionality is possible.

As shown in FIG. 2, app network 212 contains one or more apps and may be called upon to download or provide one or more of these apps to Internet of Things device 208 and/or wearable device 204. App network 212 may comprise app network software 278, which governs the communications and the choice of download. App database 280, which contains the apps themselves, can be similar to Internet of Things device app database 276, and the API 282 can translate those apps into a form, or language, that the wearable device 204 may use. If wearable device 204 is capable of using extended wearable device language, operating system, or protocol, then the API 282 may translate apps that may not exist in that wearable specific language or protocol into such an extended language before sending it to Internet of Things device 208 or wearable device 204. While the app network 212 is described in this embodiment as constituting a "network," it will be apparent that in other embodiments the app "network" 212 may instead be implemented in a single device, such as a server or a virtual machine in a cloud computing environment.

In operation, a user may utilize wearable device 204 to download one or more wearable apps 236 and/or an app database 232, which may come directly from app network 212 or via Internet of Things device 208. Once an app is loaded and while the user wears wearable device 204, wearable sensors 244 may record data that may then be fed into wearable apps 236. The sensor data is processed, and if wearable app 236 determines that an Internet of Things device 208 should take action based upon that data, wearable trigger program 228 may utilize the wearable communications interface 248 to send an action command to the Internet of Things device. Internet of Things device 208 trigger program may then consult device command database 274, retrieve the specific commands which must be performed by one or more actuators 1 through N 270 to effectuate the action command, and transmit those commands to one or more actuators 1 through N 270.

Figure 3:
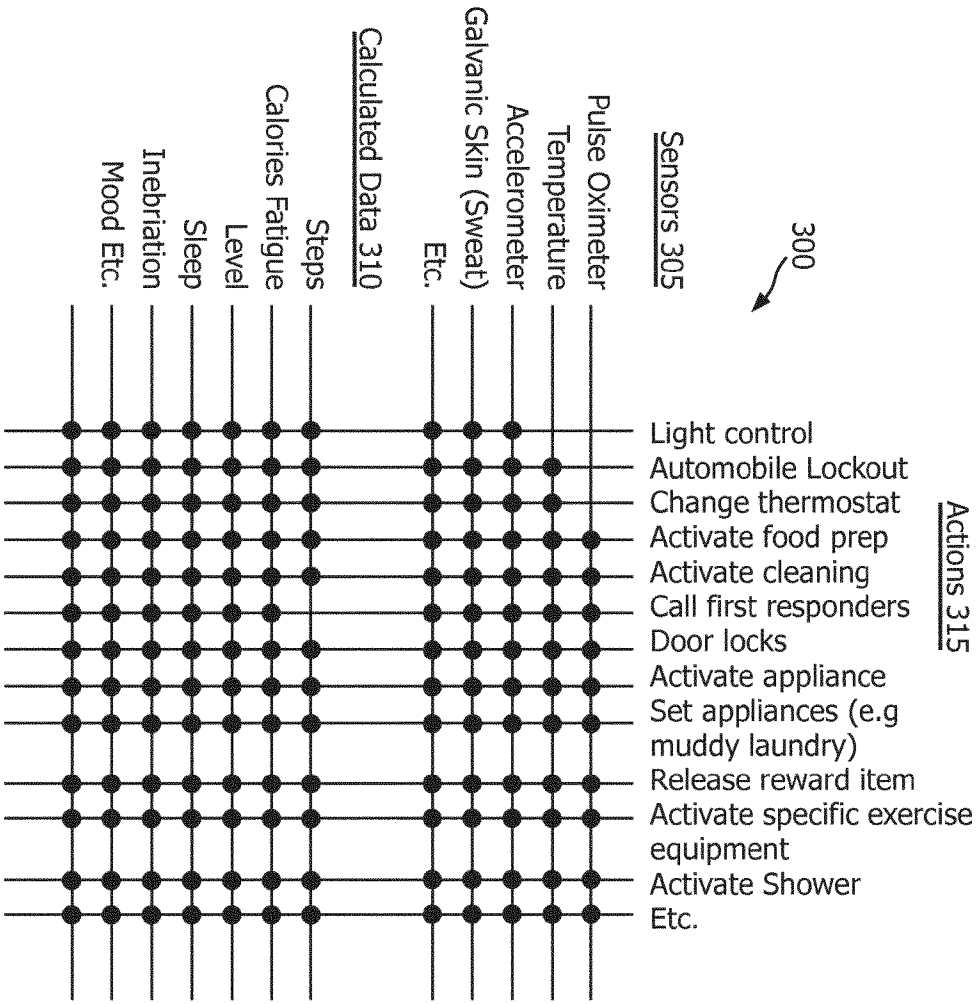
FIG. 3 is an example matrix of sensor data and calculated data and actions that can be associated with the data, in accordance with an embodiment.

Referring to FIG. 3, in one embodiment, is an exemplary matrix 300 of sensor data 305, calculated data 310, and actions 315 that can be associated with one or both of each. The sensor data and calculated data is data determined by one or more wearable sensors 244 and/or calculated directly therefrom. For example, the "Accelerometer" sensor data 305 shown in FIG. 3 corresponds to an accelerometer that records movement of a wearable device. Calculated data 310 can be calculated directly from that accelerometer data, including but not limited to a number of steps taken, if the wearable is acting like a pedometer, and/or calories burned, which can be determined by taking the number of steps data and applying one or more mathematical algorithms. Listed along one side of the matrix are actions 315 that may be taken in response to the sensor data and/or the calculated data. Each black dot indicates where a sensor and/or calculated data may lead to an action. For example, a pulse oximeter sensor may cause actions such as activating food preparation, activating cleaning of a space, calling first responders, locking or unlocking doors, activating one or more appliances, and/or setting one or more appliances. As another example, if a wearer has been exercising, their clothing may need to be washed more rigorously than it might otherwise. In some embodiments, the pulse oximeter data may be associated with a reward item if the user chooses to use a system of rewards. In some embodiments, actions may activate specific exercise equipment. For example, a treadmill may attempt to keep a user at a certain heart rate by speeding up or slowing down. Further, actions may activate a shower. For example, as described further herein, when a user finishes exercising their heart rate decreases, so a decrease in heart rate may correspond to an action that turns on the user's shower.

Similarly, with calculated data, inebriation can be measured from accelerometer data, galvanic skin data, and/or others, and one or more corresponding actions may activate light control to dim lights in the case of a hangover, lock out a user's automobile once they have had too much to drink, change a thermostat setting in order to help wake up a user, activate food preparation or cleaning, and/or call first responders, depending on the level of inebriation and/or other factors. In some embodiments, actions may unlock doors to assist an inebriated user in getting home safely, activate an appliance, set appliance settings, release a reward item, activate specific exercise equipment or a shower, etc. It should be noted that the sensors, calculated data, and actions contained in the matrix of FIG. 3 are not exhaustive, as the matrix is merely a representative sample of the types of sensor/action correspondences that could be created.

FIG. 4 shows an example of a wearable sensor database 252, which contains data reported by one or more wearable sensors 244. The first column specifies the sensor, which is the identity of the wearable sensor that recorded the data. In this case, two examples are given, the pulse oximeter and the accelerometer. The next column is the data type; this is the specific type of data recorded by each sensor. As shown, each sensor may in some embodiments record two or more different types of data; a pulse oximeter may report both pulse and blood pressure, while an accelerometer may report motion data and steps data derived from the motion data. The third and fourth columns specify the date and time of the sensor recording, and the fifth column specifies the actual datum, i.e., the unique data drawn from each of the sensors. As shown, the pulse oximeter may record a pulse of 99 beats per minute or "bpm" in the first row and a blood pressure of 110 over 80. On the other hand, the accelerometer may record motion by saving data or a link to a data file specifying such motion, which illustrates that in some cases data files may be recorded instead of or in addition to unique datums. The accelerometer also shows a reading for steps of 268, which shows that this data can also be additive, where the next sensor information recorded may be 268 plus however many steps were taken since 11:15.

Figure 5:
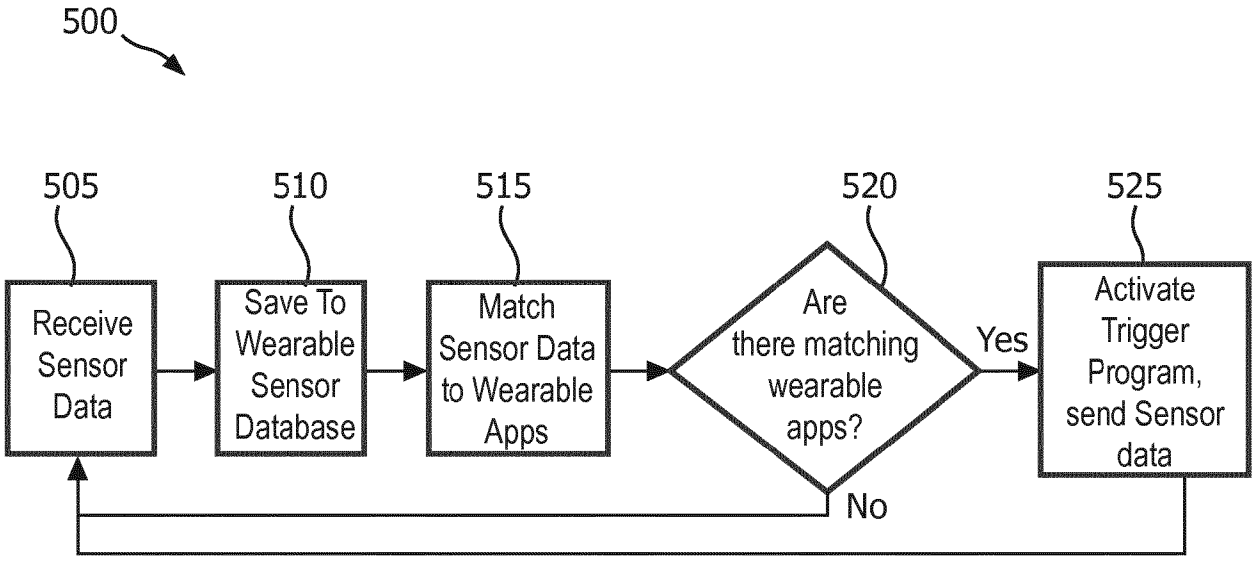
FIG. 5 is a flow diagram illustrating wearable base software, in accordance with an embodiment.

Referring to FIG. 5, in one embodiment, is an exemplary method 500 that wearable base software 224 may be configured to perform. In this example, method 500 begins by receiving sensor data from one or more wearable sensors 244 and/or tethered sensors at step 505. Next, at step 510, method 500 may save the sensor data to wearable sensor database 252, as shown in FIG. 4. Next, at step 515, method 500 may match sensor data to wearable apps 236; as described further in the context of FIG. 6 below, wearable app match database 256 can be used for that purpose. Next, method 500 may execute a decision step at step 520: are there matching wearable apps? If no, method 500 may return to step 505. If yes, method 500 may proceed to step 525 and activate trigger program 266 with the sensor data as an input. After trigger program 266 is activated, method 500 may return to step 505.

Referring to FIG. 6, in one embodiment, is an example of wearable app match database 256, which can be used to match data types with specific wearable apps 236. The first column is the data type; in this example, there are two possibilities shown: the first is sleep and the second is for accelerometer and pulse data. The next column is the wearable app associated with the data type; these correspond to the wearable apps 1 through N 236 that are associated with the data types shown in the first column. As shown, information related to a NoDoze Driving app and a Shower Starter app may be included in wearable app match database 256. The third column shows the wearable app file name, which may be the location on wearable device 204 in memory where that specific app can be found. The fourth column specifies one or more Internet of Things devices that will receive an action command from the wearable app. As shown, the NoDoze Driving app is associated with the user's Ford 150 truck that has a certain serial number, and the Shower Starter app is associated with the Delta Spa system with its serial number. The fifth column specifies action commands that will be sent by the wearable app one or more of various corresponding terms or requirements are met. For example, the NoDoze Driving app may send an action command to lock out the car when a user is determined to be sleepy, while the Shower Starter may send an action command to start a post-workout shower. Although not shown in FIG. 6, it is possible that an app may have more than one related action command, depending on the exact data it is receiving. Accordingly, for example, a NoDoze Driving app may lock out a car initially when a user is sleepy, but then after the user has slept for a certain amount of time, as determined by the sleep data, the app may unlock the car.

Example System Architecture for a Wearable Device

Figure 7:
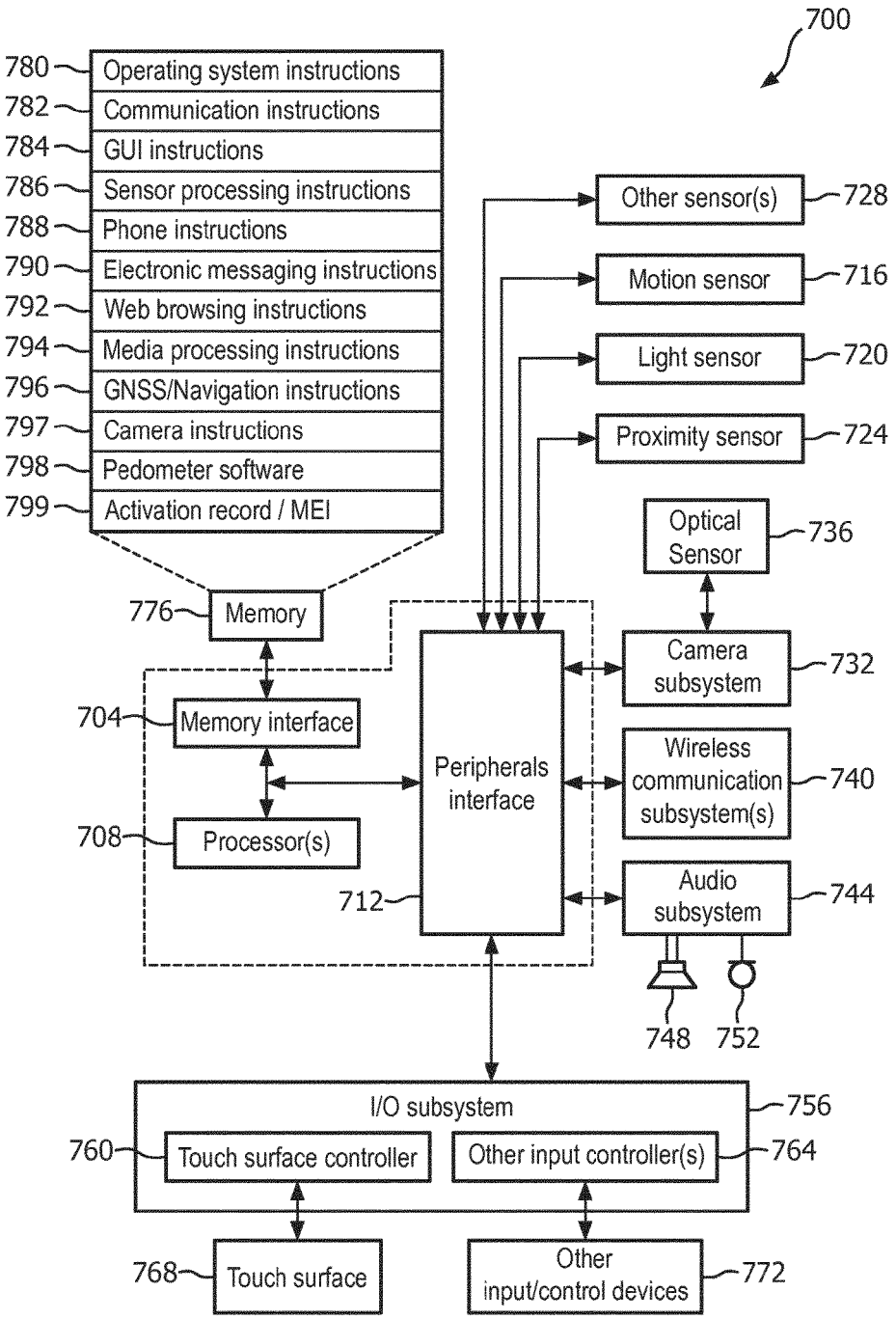
FIG. 7 is an schematic representation of a wearable device, in accordance with an embodiment.

Referring to FIG. 7, in one embodiment, is a schematic representation of an exemplary wearable computing device 700 that may be configured to implement any one or more of various features and/or processes of the present disclosure, such as the features and processes illustrated in other figures of this disclosure, as well as features and processes that would be apparent to those of ordinary skill in the art after reading this entire disclosure. As shown, computing device 700 may include a memory interface 704, one or more data processors, image processors and/or central processing units 708, and a peripherals interface 712. Memory interface 704, one or more processors 708, and/or peripherals interface 712 may be separate components or may be integrated in one or more integrated circuits. The various components in computing device 700 may be coupled by one or more communication buses or signal lines.

Sensors, devices, and subsystems may be coupled to peripherals interface 712 to facilitate one or more functionalities. For example, a motion sensor 716, a light sensor 720, and a proximity sensor 724 may be coupled to peripherals interface 712 to facilitate orientation, lighting, and/or proximity functions. Other sensors 728 may also be connected to peripherals interface 712, such as a global navigation satellite system (GNSS) (e.g., GPS receiver), a temperature sensor, a biometric sensor, and/or one or more other sensing devices, to facilitate related functionalities.

A camera subsystem 732 and an optical sensor 736, e.g., a charged coupled device (CCD) or a complementary metal-oxide semiconductor (CMOS) optical sensor, may be utilized to facilitate camera functions, such as recording images and/or video. Camera subsystem 732 and optical sensor 736 may be used to collect images of a user to be used during authentication of a user, e.g., by performing facial recognition analysis.

Communication functions may be facilitated through one or more wireless communication subsystems 740, which may include radio frequency receivers and transmitters and/or optical (e.g., infrared) receivers and transmitters. The specific design and implementation of communication subsystem 740 may depend on the communication network(s) over which computing device 700 is intended to operate. For example, computing device 700 may include communication subsystems 740 designed to operate over a GSM network, a GPRS network, an EDGE network, a Wi-Fi™ or WiMax™ network, and/or a Bluetooth™ network. In particular, wireless communication subsystems 740 may include hosting protocols such that one or more devices 700 may be configured as a base station for other wireless devices.

An audio subsystem 744 may be coupled to a speaker 748 and a microphone 752 to facilitate voice-enabled functions, such as speaker recognition, voice replication, digital recording, and/or telephony functions. Audio subsystem 744 may be configured to facilitate processing voice commands, voice-printing, and voice authentication.

I/O subsystem 756 may include a touch-surface controller 760 and/or other input controller(s) 764. Touch-surface controller 760 may be coupled to a touch surface 768. Touch surface 768 and touch-surface controller 760 may, for example, detect contact and movement or a lack thereof using one or more of any of a plurality of touch sensitivity technologies, including but not limited to capacitive, resistive, infrared, and/or surface acoustic wave technologies, optionally as well as other proximity sensor arrays and/or other elements for determining one or more points of contact with touch surface 768.

Other input controller(s) 764 may be coupled to other input/control devices 772, such as one or more buttons, rocker switches, thumb-wheel, infrared port, USB port, and/or a pointer device such as a stylus. One or more related buttons or other controls (not shown) may include one or more sets of up/down buttons for volume and/or amplitude control of speaker 748 and/or microphone 752. Using the same or similar buttons or other controls, a user may activate a voice control, or voice command, module that enables the user to speak commands into microphone to cause device 700 to execute the spoken command. The user may customize functionality of one or more buttons or other controls. Touch surface 768 may, for example, also be used to implement virtual or soft buttons and/or a keyboard.

In some implementations, computing device 700 may present recorded audio and/or video files, such as MP3, AAC, and/or MPEG files. In some implementations, computing device 700 may include the functionality of an MP3 player, such as an iPod™. Computing device 700 may, therefore, include a 36-pin connector that is compatible with related iPod™ hardware. Other input/output and control devices may also be used.

As shown, memory interface 704 may be coupled to one or more types of memory 776. Memory 776 may include high-speed random access memory and/or non-volatile memory, such as one or more magnetic disk storage devices, one or more optical storage devices, and/or flash memory (e.g., NAND, NOR). Memory 776 may store an operating system 780, such as Darwin™, RTXC, LINUX, UNIX, OS X™, WINDOWS™, and/or an embedded operating system such as VxWorks. Operating system 780 may include instructions for handling basic system services and/or for performing hardware dependent tasks. In some implementations, operating system 780 may comprise a kernel (e.g., UNIX kernel). Further, in some implementations, operating system 780 may include instructions for performing voice authentication.

Memory 776 may also store communication instructions 782 to facilitate communicating with one or more additional devices, one or more computers, and/or one or more servers. Additionally or alternatively, memory 776 may include: graphical user interface instructions 784 to facilitate graphic user interface processing; sensor processing instructions 786 to facilitate sensor-related processing and functions; phone instructions 788 to facilitate phone-related processes and functions; electronic messaging instructions 790 to facilitate electronic-messaging related processes and functions; web browsing instructions 792 to facilitate web browsing-related processes and functions; media processing instructions 794 to facilitate media processing-related processes and functions; GNSS/Navigation instructions 796 to facilitate GNSS and navigation-related processes and instructions; and/or camera instructions 797 to facilitate camera-related processes and functions. Memory 776 may store other software instructions 798 to facilitate other processes and functions. For example, other software instructions 798 may include instructions for counting steps the user takes when device 700 is worn.

Memory 776 may also store other software instructions (not shown), such as web video instructions to facilitate web video-related processes and functions and/or web shopping instructions to facilitate web shopping-related processes and functions. In some implementations, media processing instructions 794 may be divided into audio processing instructions and video processing instructions to facilitate audio processing-related processes and functions and video processing-related processes and functions, respectively. An activation record and International Mobile Equipment Identity (IMEI) 799 or similar hardware identifier may also be stored in memory 776.

Each of the above identified instructions and applications may correspond to a set of instructions for performing one or more functions described herein. These instructions need not necessarily be implemented as separate software programs, procedures, or modules. Memory 776 may include additional instructions or fewer instructions. Further, various functions of computing device 700 may be implemented in hardware and/or in software, including in one or more signal processing and/or application specific integrated circuits.

Figure 8A:
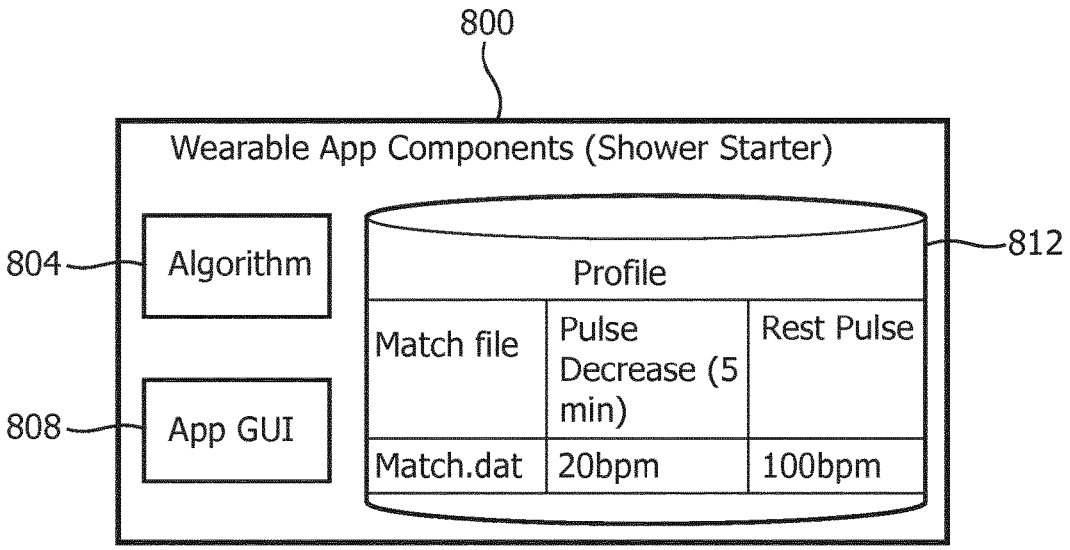
FIG. 8A is a schematic representation of a wearable device, in accordance with an embodiment.
Figure 8B:
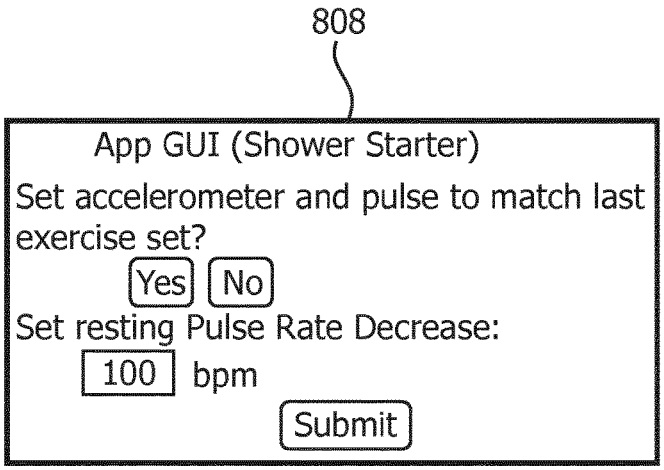
FIG. 8B is an example of a wearable device graphical user interface, in accordance with an embodiment.
Figure 8C:
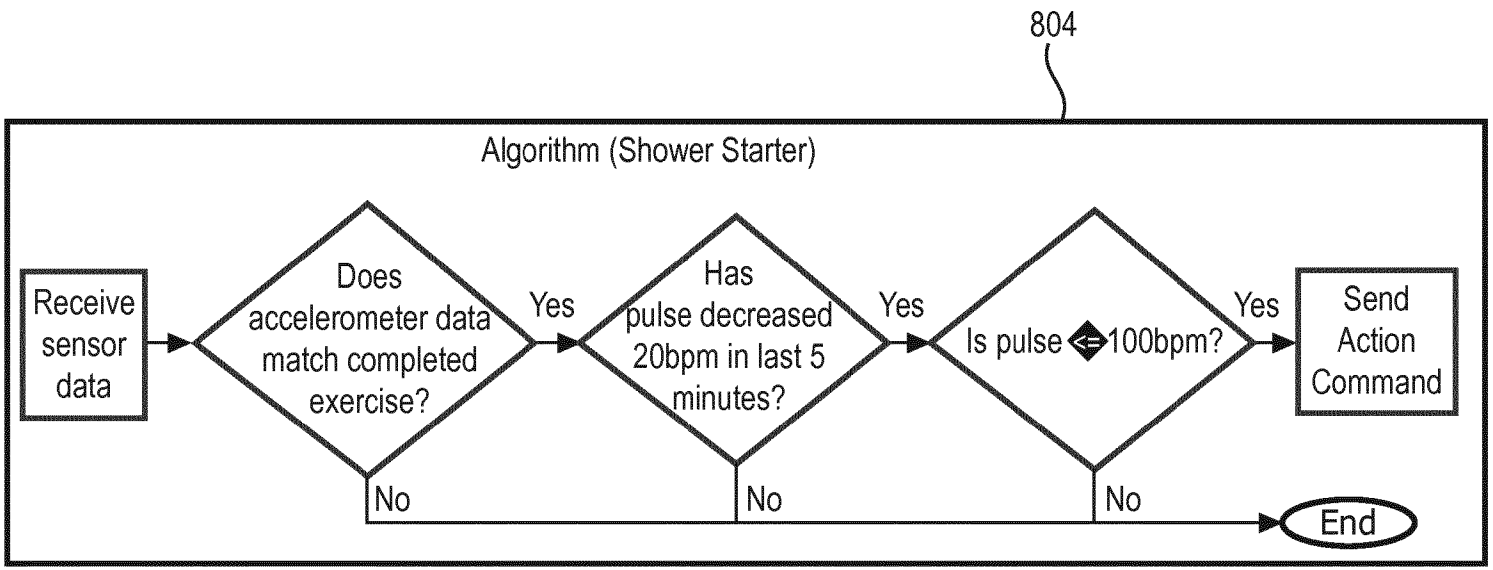
FIG. 8C is a flow diagram illustrating a wearable device algorithm, in accordance with an embodiment.

Referring to FIG. 8A, in one embodiment, is a schematic representation of the components 800 of the wearable app, in this case showing details of the Shower Starter app. Within the wearable app there is an algorithm 804, which is described further in the context of FIG. 8C, and an app GUI 808, an example of which is shown in FIG. 8B. The wearable app may contain a profile 812, which may comprise data that is used by the algorithm. In this case, profile 812 includes a match file (e.g., Match.dat), a pulse decrease every five minutes, which in this case is 20 beats per minute, and a rest pulse, which is 100 beats per minute. As shown in FIG. 8C and described in detail below, the profile data can be utilized by algorithm 804.

Referring to FIG. 8B, in one embodiment, is an example of app GUI 808, which the user may use to either set or modify the information shown in the profile, among other information. As shown, GUI 808 may include an inquiry asking the user whether they wish to set accelerometer and pulse to match last exercise set, a set of yes/no buttons the user can manipulate to provide an answer to the inquiry, and a text entry field through which the user may set a resting pulse rate decrease, which may indicate the level below which their pulse rate should be considered a resting pulse rate. The App GUI 808 may further include a submit button to submit entered data to the profile.

Referring to FIG. 8C, in one embodiment, is an example algorithm 804 that can be used by a wearable app. For example, the algorithm may be utilized by the wearable app to determine whether or not to send an action command. As shown, the algorithm may begin with receiving sensor data, which is data that is sent by the wearable base software 224. Next is a decision step: does the accelerometer data match the completed exercise? The answer to this decision may be determined as a function of a match file stored in the profile in the wearable app, in this example "Match.dat." If a match is found, then the user has completed their exercise set and they proceed to the next step. If there is no match, the algorithm may end. As shown, the next step may be a decision step: has pulse decreased 20 beats per minute in the last five minutes? Such a decrease may correspond to the user starting to cool off from their exercise routine. If the answer is yes, the algorithm may proceed to the next step. If not, the algorithm may end. At the next step, the algorithm may determine: is the pulse less than or equal to 100 beats per minute? That is, is the user done cooling off and about to go upstairs? If the answer is yes, then the wearable app may send the action command like the action command found in FIG. 6, which may start a post-workout shower. Again, if the answer is no, then the algorithm may end.

Figure 9:
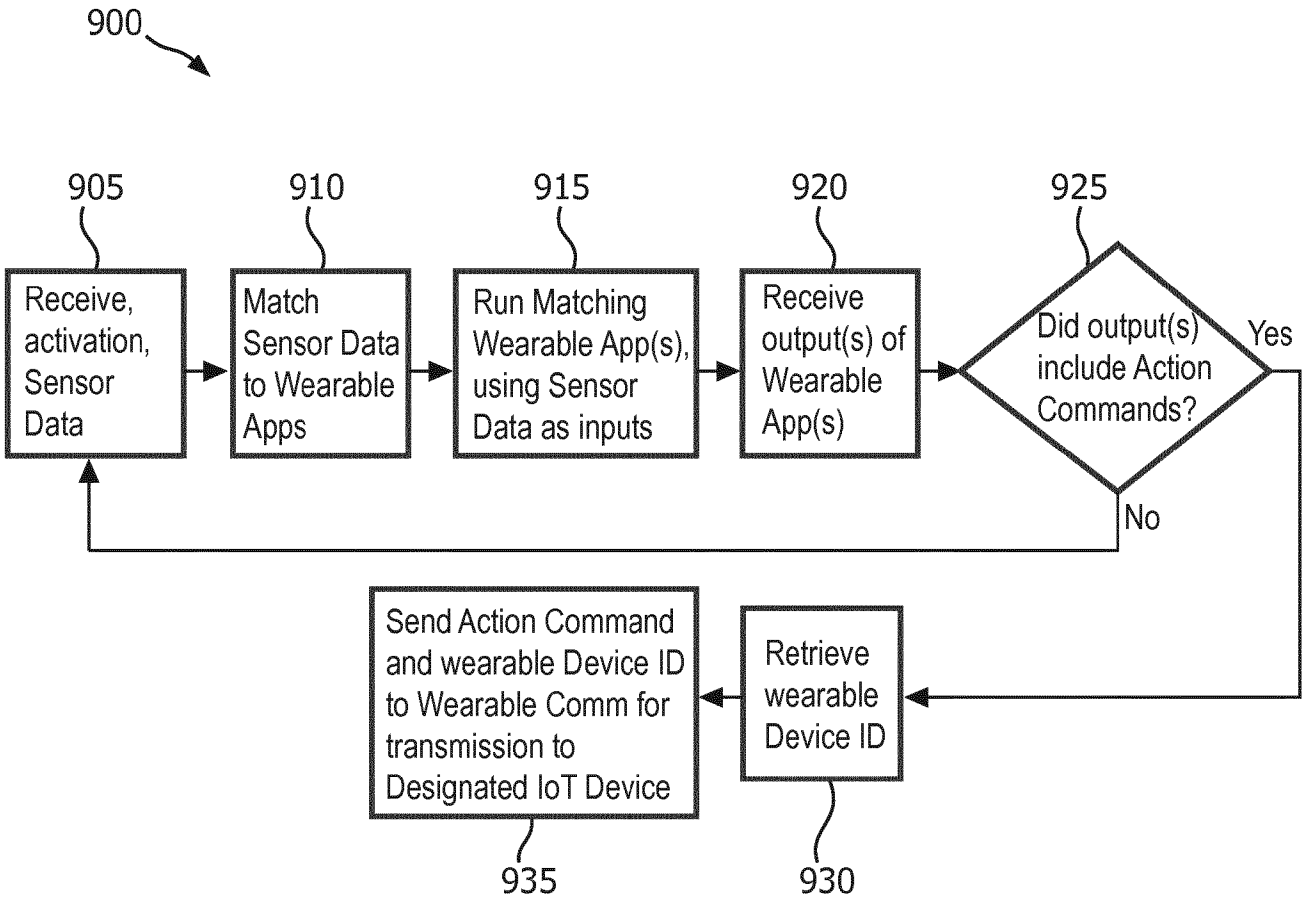
FIG. 9 is a flow diagram illustrating a wearable device algorithm, in accordance with an embodiment.

Referring to FIG. 9, in one embodiment, is an exemplary method 900 that wearable trigger program 228 may be configured to perform, which may determine whether the wearable app should be run and, based on that output, whether data should be sent to an Internet of Things device 208. In this example, method 900 begins at step 905 by receiving activation and sensor data from base software of the wearable device 204. Next, method 900 may, at step 910, match sensor data to wearable apps 236, which may involve the same functionality of the match sensor data to wearable apps step 515 of FIG. 5. At this step, the sensor data that is received may be matched to the wearable apps found in wearable app match database 256 to determine which, if any, wearable apps should be run. Next, method 900 may run one or more matching wearable apps using sensor data as inputs, the apps being specified by the file names in wearable app match database 256. Next, at step 920, method 900 may receive one or more outputs of wearable apps 236, which, in this case, would be action commands. Next, method 900 may, at step 925, execute the decision step: did the outputs include action commands? If the answer is no, method 900 may return to step 905. If the answer is yes, then method 900 may advance to step 930, which involves retrieving the wearable device ID 240. Method 900 may then send the action command and wearable device ID 240 to wearable communication interface 248 at step 935 for transmission to a designated Internet of Things device 208, as designated in the wearable app match database 256.

Figure 10:
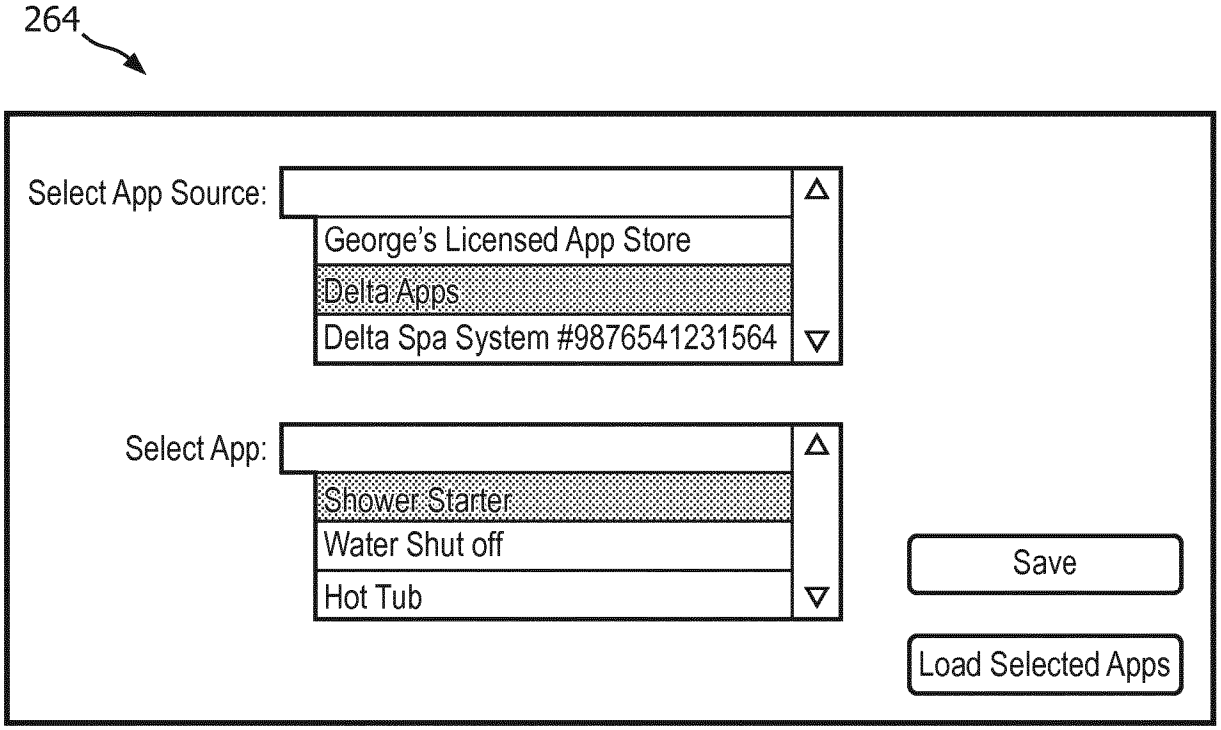
FIG. 10 is an example of a wearable device graphical user interface, in accordance with an embodiment.

Referring to FIG. 10, in one embodiment, is an example of a wearable GUI 264, which in this example contains two drop-down menus. The first drop-down menu enables a user to select the app source, which is the source of the app the user wishes to download to their wearable device 204. Such app sources may include, for example, George's Licensed App Store, which is a third party app store, Delta Apps, which is the manufacturer of an Internet of Things device 208, and Delta Spa system number 9876541231564, which is an Internet of Things device itself from which wearable device 204 may download one or more wearable apps 236. In this case, Delta Apps is selected, so the next drop-down menu asks the user to select an app from that app source. In this example, three apps are shown in the menu: Shower Starter, Water Shut off, and Hot Tub, and the user has selected Shower Starter. There are also two soft-selection buttons shown: a save button, which a user may use to save their current preferences, and a load selected apps button, which a user may use to download the selected apps.

Figure 11:
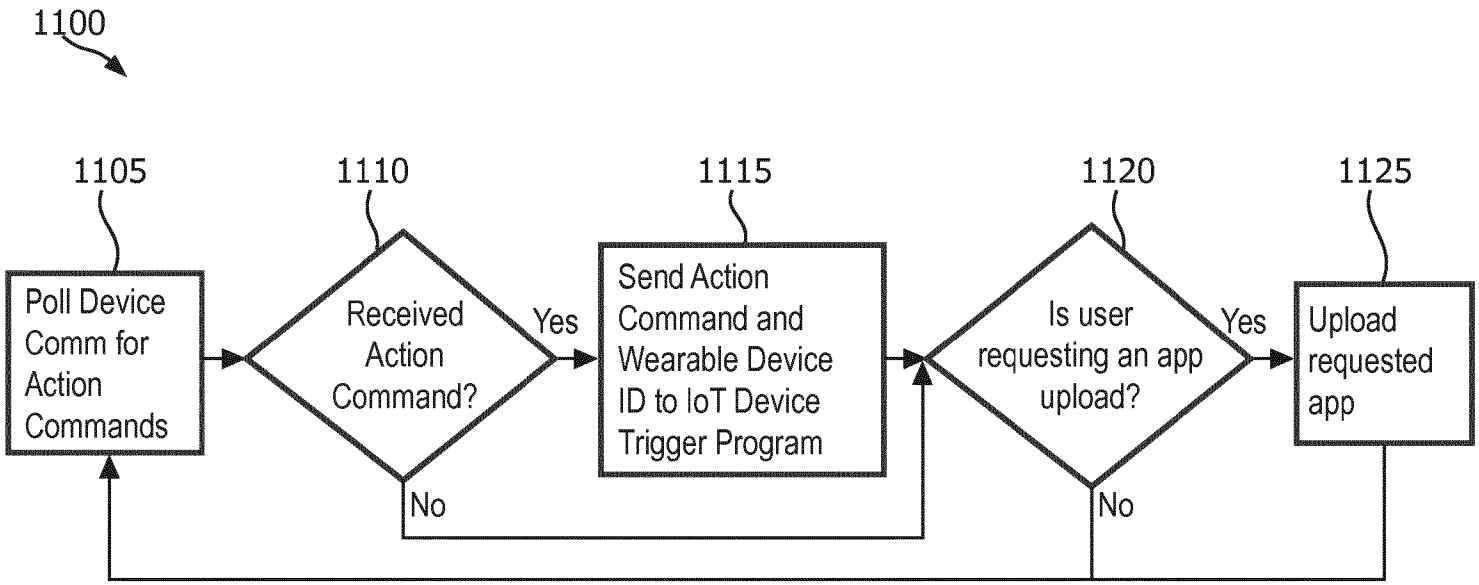
FIG. 11 is a flow diagram of an Internet of Things device base program, in accordance with an embodiment.

Referring to FIG. 11, in one embodiment, is an exemplary method 1100 that Internet of Things device base software 268 may be configured to perform. In this example, method 1100 begins at step 1105 by polling the device communication interface 272 of Internet of Things device 208 for action commands. Next, at step 1110, method 1100 may execute a decision step: received action command? That is, has an action command been received? If yes, then method 1100 may proceed to step 1115, i.e., send the action command and wearable device ID 240 to Internet of Things device trigger program 266. If no, then method 1100 may skip step 1115. Method 1100 may then proceed to step 1120 and inquire: is the user requesting an app upload from the device? If the answer is no, method 1100 may return to step 1105. If the answer is yes, then method 1100 may proceed to step 1125 and upload the requested app.

Figures 12, 13:
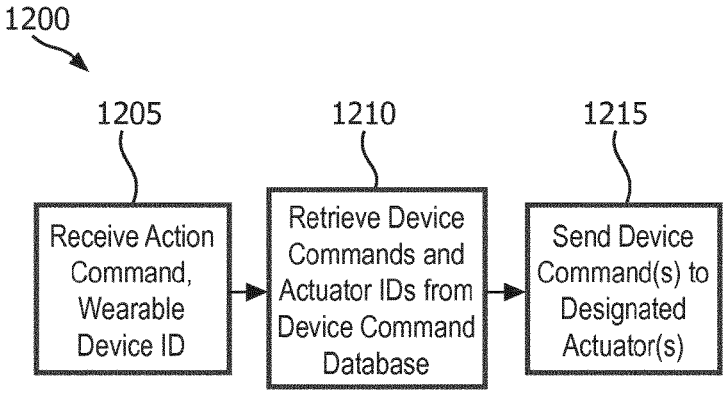
FIG. 12 is a flow diagram of an Internet of Things device trigger program, in accordance with an embodiment.
FIG. 13 is an example of an Internet of Things device command database, in accordance with an embodiment.

Referring to FIG. 12, in one embodiment, is an exemplary method 1200 that Internet of Things device trigger program 266 may be configured to perform, which may be activated as a result of the middle step of FIG. 11. In this example, method 1200 begins at step 1205 by receiving the action command and the wearable ID from the base software and then, at step 1210, retrieving the device commands and actuator IDs from a device command database 274, which is further described in the context of FIG. 13. Method 1200 may then proceed to step 1215 and send the device commands to the designated actuators 270.

Referring to FIG. 13, in one embodiment, is an example of an Internet of Things device command database 274, which allows the Internet of Things device 208 to receive an action command from a wearable device 204 and translate it into specific commands for specific actuators 270. In this case, the database includes the device commands associated with the action command "start post-workout shower" from wearable device JC4567. If the device, which in this case may be the Delta Spa mentioned previously, receives that action command, then it may activate two device commands, one each for two different actuators 270. For example, the first device command may issue a "start now" command to an in-line hot water heater, which may cause the water heater to start heating up, and the second device command may issue a "start in five minutes" command to the shower faucet. Notably, in this case, the Internet of Things shower faucet and in-line water heater are both part of a smart spa. Thus, in this example, when wearable device 204 sends the "start post-workout shower" action command, Internet of Things device 208 will immediately start the hot water heating and in five minutes will start the shower so that the user may come up from their exercise, disrobe, and immediately step into a hot shower.

Figure 14:
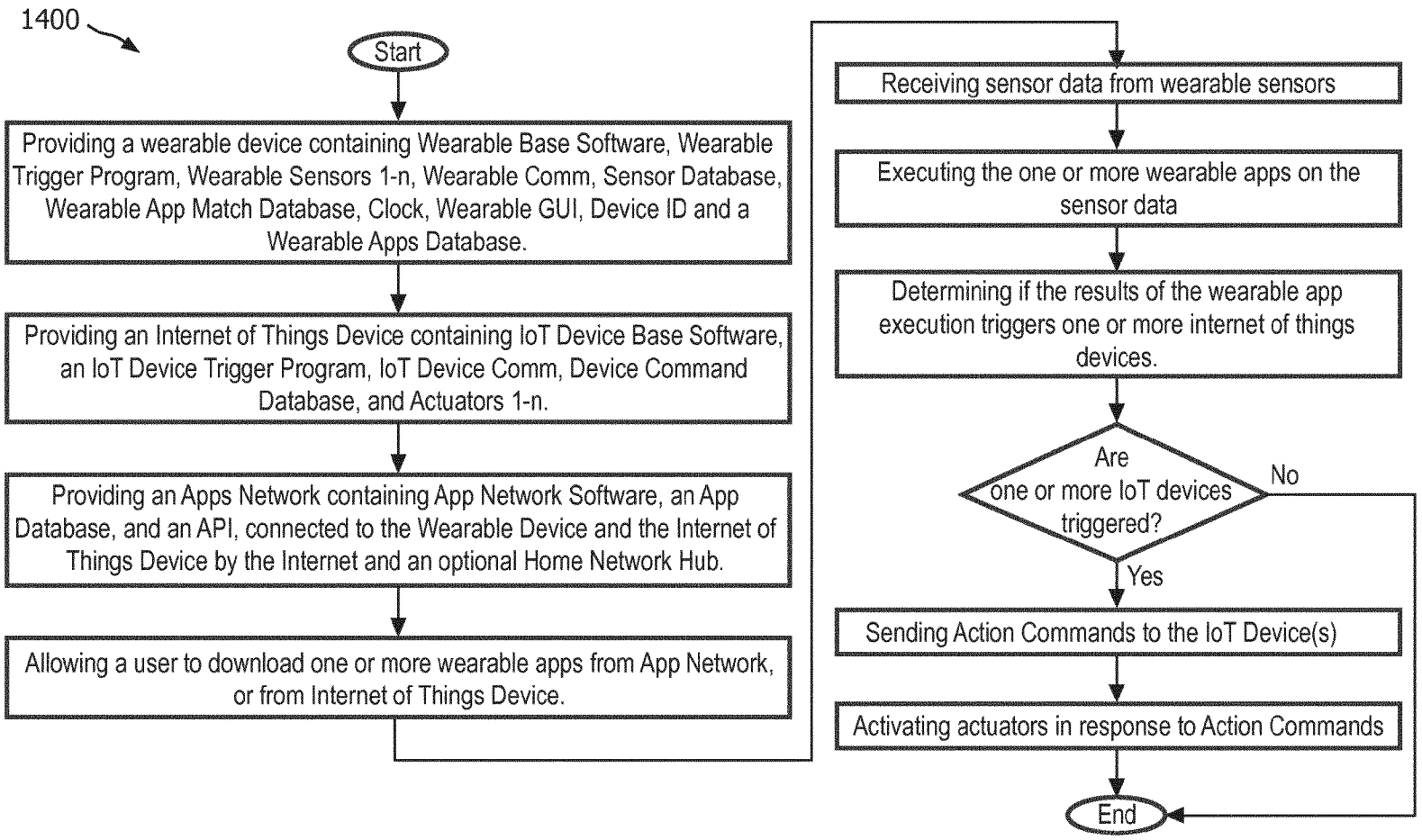
FIG. 14 is a flow chart of a method implemented in the context of a wearable health interface for controlling Internet of Things devices, in accordance with an embodiment.

Referring to FIG. 14, in one embodiment, is an example of a method 1400 that can be implemented in the context of a wearable health interface for controlling Internet of Things devices. Such a method may begin with providing a wearable device 204 containing wearable base software 224, a wearable trigger program 228, one or more wearable sensors 1 through N 244, a wearable communication interface 248, a sensor database, a wearable app match database 256, a clock 260, a wearable GUI 264, a device ID 240, and a wearable apps database 232. Next, the method may involve providing an Internet of Things device 208 containing Internet of Things base software, an Internet of Things device trigger program 266, an Internet of Things device communication interface, a device command database 274, and one or more actuators 1 through N 270. Next, the method may involve providing an app network 212 containing app network software 278, an app database 280, and an API 282, the app network being connected to wearable device 204 and Internet of Things device 208 by the Internet 216 and/or an optional home network hub 220. Next, the method may involve allowing the user to download one or more wearable apps 236 form the app network 212 or from the Internet of Things device 208. Next, the method may involve receiving sensor data from one or more wearable sensors 244 and then executing one or more wearable apps 236 as a function of the sensor data. The method may then involve determining whether the results of the wearable app execution triggers one or more Internet of Things devices and then determining whether one or more Internet of Things devices are triggered. If the answer is no, the method may terminate. If the answer is yes, the method may proceed to the next step, which may entail sending action commands to the Internet of Things device 208 or devices and then activating actuators 270 in response to action commands.

Figure 15:
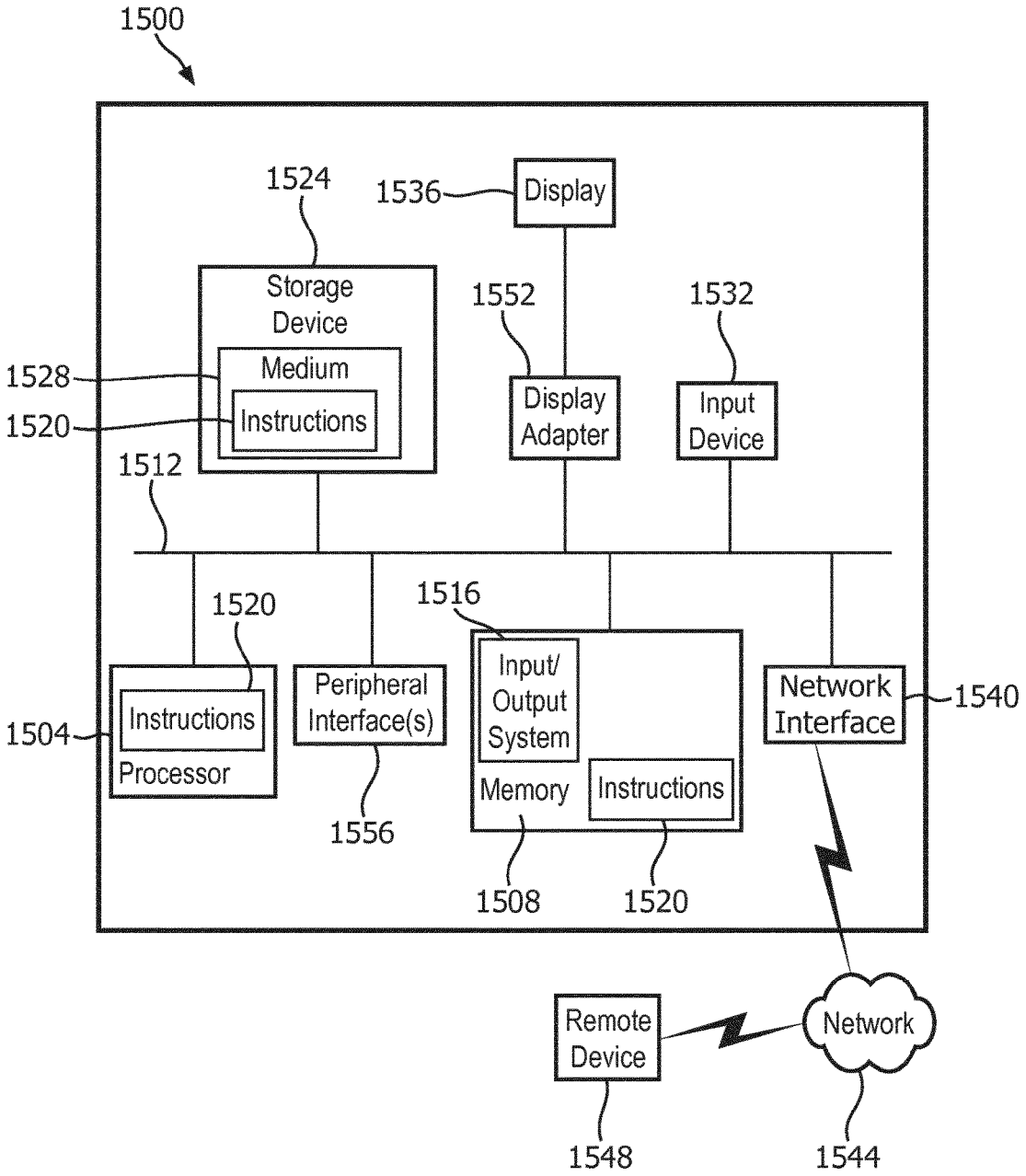
FIG. 15 is a schematic representation of a computing system for utilizing a wearable health interface to control one or more Internet of Things devices, in accordance with an embodiment.

Referring to FIG. 15, in one embodiment, is a diagrammatic representation of one embodiment of a computing device in the exemplary form of a computer system 1500 within which a set of instructions for causing a control system, such as any one or more of various systems of the present disclosure, including the systems illustrated in other figures of this disclosure as well as systems that would be apparent to those of ordinary skill in the art after reading this entire disclosure, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure.

According to an embodiment, computer system 1500 includes a processor 1504 and a memory 1508 that communicate with each other, and with other components, via a bus 1512. Bus 1512 may include any of several types of bus structures including, but not limited to, a memory bus, a memory controller, a peripheral bus, a local bus, and any combinations thereof, using any of a variety of bus architectures. Memory 1508 may include various components (e.g., machine-readable media) including, but not limited to, a random access memory component, a read only component, and any combinations thereof. In one example, a basic input/output system 1516 (BIOS), including basic routines that help to transfer information between elements within computer system 1500, such as during start-up, may be stored in memory 1508. Memory 1508 may also include (e.g., stored on one or more machine-readable media) instructions (e.g., software) 1520 embodying any one or more of the aspects and/or methodologies of the present disclosure. In another example, memory 1508 may further include any number of program modules including, but not limited to, an operating system, one or more application programs, other program modules, program data, and any combinations thereof.

Computer system 1500 may also include a storage device 1524. Examples of a storage device (e.g., storage device 1524) include, but are not limited to, a hard disk drive, a magnetic disk drive, an optical disc drive in combination with an optical medium, a solid-state memory device, and any combinations thereof. Storage device 1524 may be connected to bus 1512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1524 (or one or more components thereof) may be removably interfaced with computer system 1500 (e.g., via an external port connector (not shown)). Particularly, storage device 1524 and an associated machine-readable medium 1528 may provide nonvolatile and/or volatile storage of machine-readable instructions, data structures, program modules, and/or other data for computer system 1500. In one example, software 1520 may reside, completely or partially, within machine-readable medium 1528. In another example, software 1520 may reside, completely or partially, within processor 1504.

Computer system 1500 may also include an input device 1532. In one example, a user of computer system 1500 may enter commands and/or other information into computer system 1500 via input device 1532. Examples of an input device 1532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1532 may be interfaced to bus 1512 via any of a variety of interfaces (not shown) including, but not limited to, a serial interface, a parallel interface, a game port, a USB interface, a FIREWIRE interface, a direct interface to bus 1512, and any combinations thereof. Input device 1532 may include a touch screen interface that may be a part of or separate from display 1536, discussed further below. Input device 1532 may be utilized as a user selection device for selecting one or more graphical representations in a graphical interface as described above.

A user may also input commands and/or other information to computer system 1500 via storage device 1524 (e.g., a removable disk drive, a flash drive, etc.) and/or network interface device 1540. A network interface device, such as network interface device 1540, may be utilized for connecting computer system 1500 to one or more of a variety of networks, such as network 1544, and one or more remote devices 1548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1544, may employ a wired and/or a wireless mode of communication. In general, any network topology may be used. Information (e.g., data, software 1520, etc.) may be communicated to and/or from computer system 1500 via network interface device 1540.

Computer system 1500 may further include a video display adapter 1552 for communicating a displayable image to a display device, such as display device 1536. Examples of a display device include, but are not limited to, a liquid crystal display (LCD), a cathode ray tube (CRT), a plasma display, a light emitting diode (LED) display, and any combinations thereof. Display adapter 1552 and display device 1536 may be utilized in combination with processor 1504 to provide graphical representations of aspects of the present disclosure. In addition to a display device, computer system 1500 may include one or more other peripheral output devices including, but not limited to, an audio speaker, a printer, and any combinations thereof. Such peripheral output devices may be connected to bus 1512 via a peripheral interface 1556. Examples of a peripheral interface include, but are not limited to, a serial port, a USB connection, a FIREWIRE connection, a parallel connection, and any combinations thereof.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve various aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method for controlling an Internet of Things device via a wearable device remote from the Internet of Things device or IoT device, the method comprising the steps of:

providing a wearable device, configured to be worn or carried, that comprises a unique wearable device ID, at least one sensor, a processor, a wearable device application database[for storing one or more wearable device applications], and a communications interface;

receiving sensor data from the at least one sensor;

determining a data type of the received sensor data;

matching the received sensor data with [the] one or more [of the] wearable device applications stored in the wearable device application database *and an application database of an application network* based on the determined data type of the received sensor data;

selecting, based on at least one match, at least one of the one or more wearable device applications [stored in the wearable device application database] to analyze the received sensor data;

analyzing the received sensor data via the selected at least one of the one or more wearable device applications by comparing the received sensor data to a predetermined trigger of a respective wearable device application of the selected at least one of the one or more wearable device applications to determine whether or not the received sensor data comprises a triggering event;

generating, if the received sensor data comprises a triggering event, one or more action command for a remote Internet of Things device; and transmitting both (i) the one or more action command and (ii) the unique wearable device ID to the remote Internet of Things device or IoT device, wherein the IoT device is configured to retrieve both (a) at least one IoT device command from an IoT device command database and (b) at least one actuator ID of one or more IoT actuator of the IoT device, in response to the transmitted one or more action command and the transmitted unique wearable device ID, *wherein the matching, selecting, analyzing, and transmitting are performed via at least the wearable device*.

2. The method of claim 1, further comprising the step of receiving, via a user interface, input regarding which of the one or more wearable device applications stored in the wearable device application database to use to analyze the received sensor data.

3. The method of claim 1, wherein the action command comprises a command to control one or more of: a light, a lock, a thermostat, a food preparation device, a cleaning device, a first responder emergency call, an appliance, a reward item, exercise equipment, and a shower.

4. The method of claim 1, wherein the at least one sensor comprises a GPS, a camera, a pulse oximeter, a temperature sensor, an accelerometer, or a galvanic skin sweat sensor.

5. The method of claim 1, further comprising the step of downloading, via [a] *the wearable* device [communication] *communications* interface, a wearable device application from [an] *the* application network to the wearable device, and storing the downloaded wearable device application in the wearable device application database.

6. The method of claim 1, further comprising the step of downloading, via [a] *the* wearable device [communication] *communications* interface, a wearable device application from an application database of the Internet of Things device to the wearable device, and storing the downloaded wearable device application in the wearable device application database.

7. A system for controlling an Internet of Things device using a wearable device remote from the Internet of Things device or IoT device, the system comprising:

an application network that comprises an application network database storing one or more wearable device applications, and a communications interface;

an Internet of Things device that comprises an application database storing one or more wearable device applications, a communications interface, and one or more actuator;

a wearable device, configured to be worn or carried, that comprises a unique wearable device ID, at least one sensor, a processor, a wearable device application database for storing one or more wearable device applications, and a communications interface, wherein the wearable device is configured to: (i) receive sensor data from the at least one sensor; (ii) determine a data type of the received sensor data; (iii) match the received sensor data with [the] one or more [of the] wearable device applications stored in the wearable device application database, *the application database of the application network, and the application database of the Internet of Things device* based on the determined data type of the received sensor data; (iv) select, based on at least one match, at least one of the one or more wearable device applications [stored in the wearable device application database] to analyze the received sensor data; (v) analyze the received sensor data via the selected at least one of the one or more wearable device applications by comparing the received sensor data to a predetermined trigger of a respective wearable device application of the selected at least one of the one or more wearable device applications to determine whether or not the received sensor data comprises a triggering event; (vi) generate, if the received sensor data comprises a triggering event, one or more action command for the Internet of Things device; and (vii) transmit both (a) the one or more action command and (b) the unique wearable device ID to the Internet of Things device or IoT device, wherein the IoT device is configured to retrieve both (c) at least one IoT device command from an IoT device command database and (d) at least one actuator ID for one or more IoT actuator of the IoT device, in response to the transmitted one or more action command and the transmitted unique wearable device ID, *wherein the match, select, analyze, generate and transmit are performed via at least the wearable device*.

8. The system of claim 7, wherein the wearable device is further configured to establish, via [a] *the* wearable device [communication] *communications* interface, communication with the application network, and to download a wearable device application from the application network database and store the downloaded wearable device application in the wearable device application database of the wearable device.

9. The system of claim 7, wherein the wearable device is further configured to establish, via [a] *the* wearable device communications interface, communication with the application database of the Internet of Things device, and to download a wearable device application from the application database of the Internet of Things device and store the downloaded wearable device application in the wearable device application database of the wearable device.

10. The system of claim 7, wherein the Internet of Things device is configured to activate an actuator, identified via a retrieved actuator ID, of the one or more actuator, in response to receiving both (i) the one or more the action command and (ii) the unique wearable device ID from the wearable device.

11. The system of claim 7, wherein the Internet of Things device is configured to determine, based on the one or more action command and the unique wearable device ID transmitted by the wearable device, whether to activate an actuator, identified via a retrieved actuator ID, of the one or more actuator, in response to receiving both (i) the one or more action command and (ii) the unique wearable device ID from the wearable device.

12. A wearable device configured to be worn or carried and to control a remote Internet of Things device, the wearable device comprising:

a unique wearable device ID;

at least one sensor;

a communications interface configured to transmit both (i) one or more action command and (ii) the unique wearable device ID to the remote Internet of Things device in response to a triggering event;

a wearable device application database for storing one or more wearable device applications; and a processor, wherein the processor is configured to: (i) receive sensor data from the at least one sensor; (ii) determine a data type of the received sensor data; (iii) match the received sensor data with the one or more of the wearable device applications of stored in the wearable device application database based on the determined type of the received sensor data; (iv) select, based on at least one match, at least one of the one or more wearable device applications stored in the wearable device application database to analyze the received sensor data; (v) analyze the received sensor data via the selected at least one of the one or more wearable device applications by comparing the received sensor data to a predetermined trigger of a respective wearable application of the selected at least one of the one or more wearable device applications to determine whether or not the received sensor data comprises a triggering event; (vi) generate, if the received sensor data comprises a triggering event, the one or more action command for the Internet of Things device; and (vii) induce the communications interface to transmit both (a) the one or more action command and (b) the unique wearable device ID to the Internet of Things device or IoT device, wherein the IoT device is configured to retrieve both (c) at least one IoT device command from an IoT device command database and (d) at least one actuator ID for one or more IoT actuator of the IoT device, in response to the transmitted one or more action command and the transmitted unique wearable device ID.

13. The wearable device of claim 12, wherein the processor is further configured to download, from an application database of the Internet of Things device, a wearable device application and store the downloaded wearable device application in the wearable device application database.

14. The wearable device of claim 12, wherein the processor is further configured to download, from an application network, a wearable device application and store the downloaded wearable device application in the wearable device application database.

*15. An Internet of Things device controllable via a wearable device remote from the Internet of Things device or IoT device, the IoT device comprising:*

*an application database storing one or more wearable device applications;*

*an IoT command database;*

*a communications interface; and*

*one or more actuator,*

*wherein the wearable device, configured to be worn or carried, comprises a unique wearable device ID, at least one sensor, a processor, a wearable device application database for storing one or more wearable device applications, and a communications interface, wherein the wearable device is configured to: (i) receive sensor data from the at least one sensor; (ii) determine a data type of the received sensor data; (iii) match the received sensor data with one or more of the wearable device applications stored in the wearable device application database. an application database of an application network. and the application database of the IoT device based on the determined data type of the received sensor data; (iv) select. based on at least one match. at least one of the one or more wearable device applications to analyze the received sensor data; (v) analyze the received sensor data via the selected at least one of the one or more wearable device applications by comparing the received sensor data to a predetermined trigger of a respective wearable device application of the selected at least one of the one or more wearable device applications to determine whether or not the received sensor data comprises a triggering event; (vi) generate. if the received sensor data comprises a triggering event. one or more action command for the Internet of Things device; and (vii) transmit both (a) the one or more action command and (b) the unique wearable device ID to the Internet of Things device or IoT device. and*

*wherein the IoT device is configured to retrieve both (i) at least one IoT device command from the IoT device command database and (ii) at least one actuator ID for one or more IoT actuator of the IoT device. in response to receiving. via the communications interface. the transmitted one or more action command and the transmitted unique wearable device ID. wherein the match. select. analyze. generate and transmit are performed via at least the wearable device.*

16. *An application network for controlling an Internet of Things device using a wearable device remote from the Internet of Things device or IoT device. the application network comprising:*

*an application database storing one or more wearable device applications;*

*a communications interface; and*

*a controller. wherein the controller is operatively coupled to the application database and the communications interface.*

*wherein the Internet of Things device comprises an application database storing one or more wearable device applications. a communications interface. and one or more actuator,*

*wherein the wearable device. configured to be worn or carried. comprises a unique wearable device ID. at least one sensor. a processor. a wearable device application database for storing one or more wearable device applications. and a communications interface. wherein the wearable device is configured to: (i) receive sensor data from the at least one sensor; (ii) determine a data type of the received sensor data; (iii) match the received sensor data with one or more of the wearable device applications stored in the wearable device application database. the application database of the application network. and the application database of the Internet of Things device based on the determined data type of the received sensor data; (iv) select. based on at least one match. at least one of the one or more wearable device applications to analyze the received sensor data; (v) analyze the received sensor data via the selected at least one of the one or more wearable device applications by comparing the received sensor data to a predetermined trigger of a respective wearable device application of the selected at least one of the one or more wearable device applications to determine whether or not the received sensor data comprises a triggering event; (vi) generate. if the received sensor data comprises a triggering event. one or more action command for the Internet of Things device; and (vii) transmit both (a) the one or*

*more action command and (b) the unique wearable device ID to the Internet of Things device or IoT device. wherein the IoT device is configured to retrieve both (c) at least one IoT device command from an IoT device command database and (d) at least one actuator ID for one or more IoT actuator of the IoT device. in response to the transmitted one or more action command and the transmitted unique wearable device ID.*

*17. The application network of claim 16. wherein the wearable device is further configured to establish. via the wearable device communications interface. communication with the application network. and to download a wearable device application from the application database of the application network and store the downloaded wearable device application in the wearable device application database of the wearable device.*

*18. The application network of claim 16. wherein the wearable device is further configured to establish. via the wearable device communications interface. communication with the application database of the Internet of Things device. and to download a wearable device application from the application database of the Internet of Things device and store the downloaded wearable device application in the wearable device application database of the wearable device.*

*19. The application network of claim 16. wherein the Internet of Things device is configured to activate an actuator. identified via a retrieved actuator ID. of the one or more actuator. in response to receiving both (i) the one or more the action command and (ii) the unique wearable device ID from the wearable device.*

*20. The application network of claim 16. wherein the Internet of Things device is configured to determine. based on the one or more action command and the unique wearable device ID transmitted by the wearable device. whether to activate an actuator. identified via a retrieved actuator ID. of the one or more actuator. in response to receiving both (i) the one or more action command and (ii) the unique wearable device ID from the wearable device.*

* * * * *